United States Patent [19]

Eisenberg et al.

[11] Patent Number: 4,862,897

[45] Date of Patent: Sep. 5, 1989

[54] ELECTROCARDIOGRAM ENHANCEMENT SYSTEM AND METHOD

[75] Inventors: Lawrence Eisenberg, New York, N.Y.; Michael A. Eisenberg, Cambridge, Mass.

[73] Assignee: Sound Enhancement Systems, Inc., New York, N.Y.

[21] Appl. No.: 948,195

[22] Filed: Dec. 31, 1986

Related U.S. Application Data

[63] Continuation-in-part of Ser. No. 914,026, Oct. 6, 1986, abandoned, which is a continuation-in-part of Ser. No. 795,059, Nov. 5, 1985, abandoned.

[51] Int. Cl.$^4$ ............................................. A61B 5/02
[52] U.S. Cl. ................................... 128/715; 128/696; 128/710
[58] Field of Search ............................... 128/660-663, 128/715, 773, 696, 710, 701; 381/67, 98; 364/417

[56] References Cited

U.S. PATENT DOCUMENTS

| | | |
|---|---|---|
| 3,267,934 | 8/1966 | Thornton . |
| 3,859,556 | 1/1975 | Schumann .......................... 315/24 |
| 3,934,267 | 1/1976 | Kosaka et al. ...................... 360/6 |
| 4,275,742 | 6/1981 | Faisandier ......................... 128/703 |
| 4,367,753 | 1/1983 | Jirak ................................. 128/708 |
| 4,483,346 | 11/1984 | Slavin .............................. 128/710 |
| 4,506,677 | 3/1985 | Lambert ........................... 128/697 |
| 4,509,526 | 4/1985 | Barnes et al. ..................... 128/663 |
| 4,534,361 | 8/1985 | Berger et al. ..................... 128/680 |
| 4,594,731 | 6/1986 | Lewkowicz ....................... 128/715 |
| 4,606,352 | 8/1986 | Geddes et al. .................... 128/702 |

OTHER PUBLICATIONS

Langner et al., "Wide Band Recording of the Electrocardiogram and Coronary Heart Disease", American Heart Journal, Sep. 1973, vol. 86, No. 3, pp. 308-317.

*Primary Examiner*—Leo P. Picard
*Attorney, Agent, or Firm*—Pennie & Edmonds

[57] ABSTRACT

An electrocardiogram enhancement system and apparatus is provided. Small amplitude, high frequency notches associated with myocardial disease and arrhythmias can be recorded by conventional chart recorders. In addition, the notches are clearly visible in the recorded waveform for visual detection and analysis of the notches by medical personnel.

In the system of the present invention electrocardiogram signals having small amplitude, high frequency notches are enhanced; first, by selectively amplifying the notches while keeping the amplitude of the remainder of the waveform constant and, second, by uniformly expanding the signal in the time domain wherein the inter-component frequency and inter-component phase relationships are maintained.

52 Claims, 10 Drawing Sheets

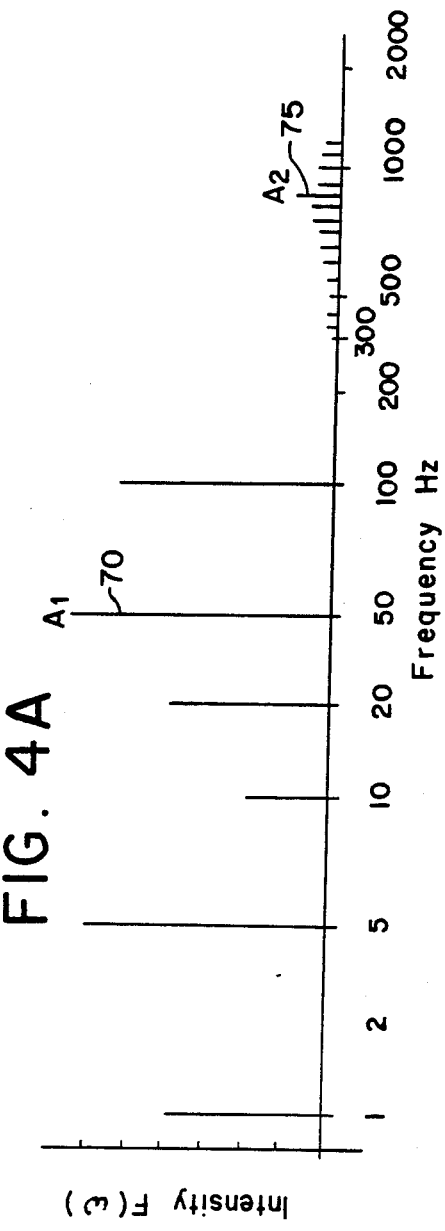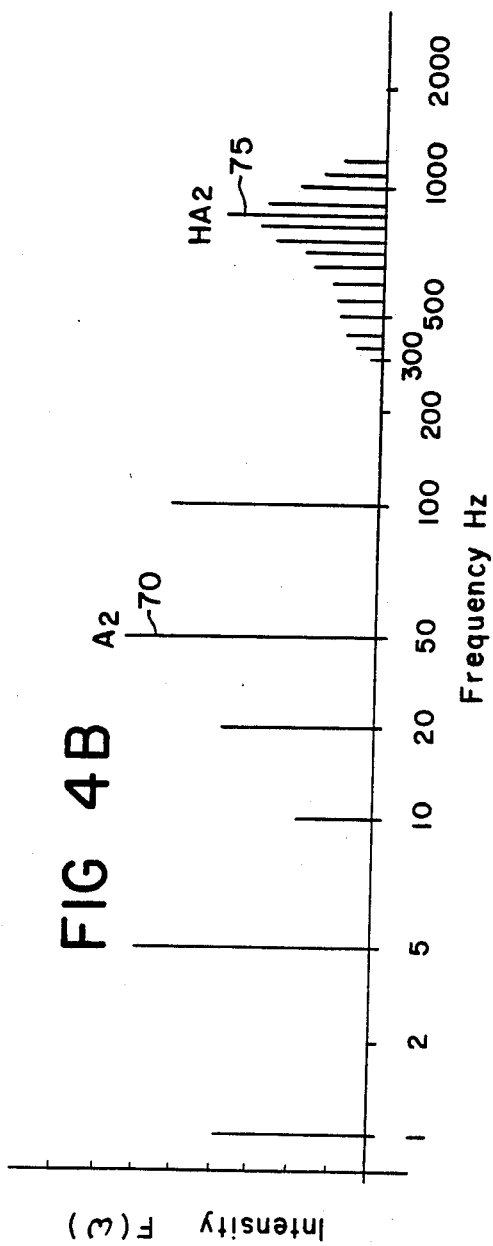

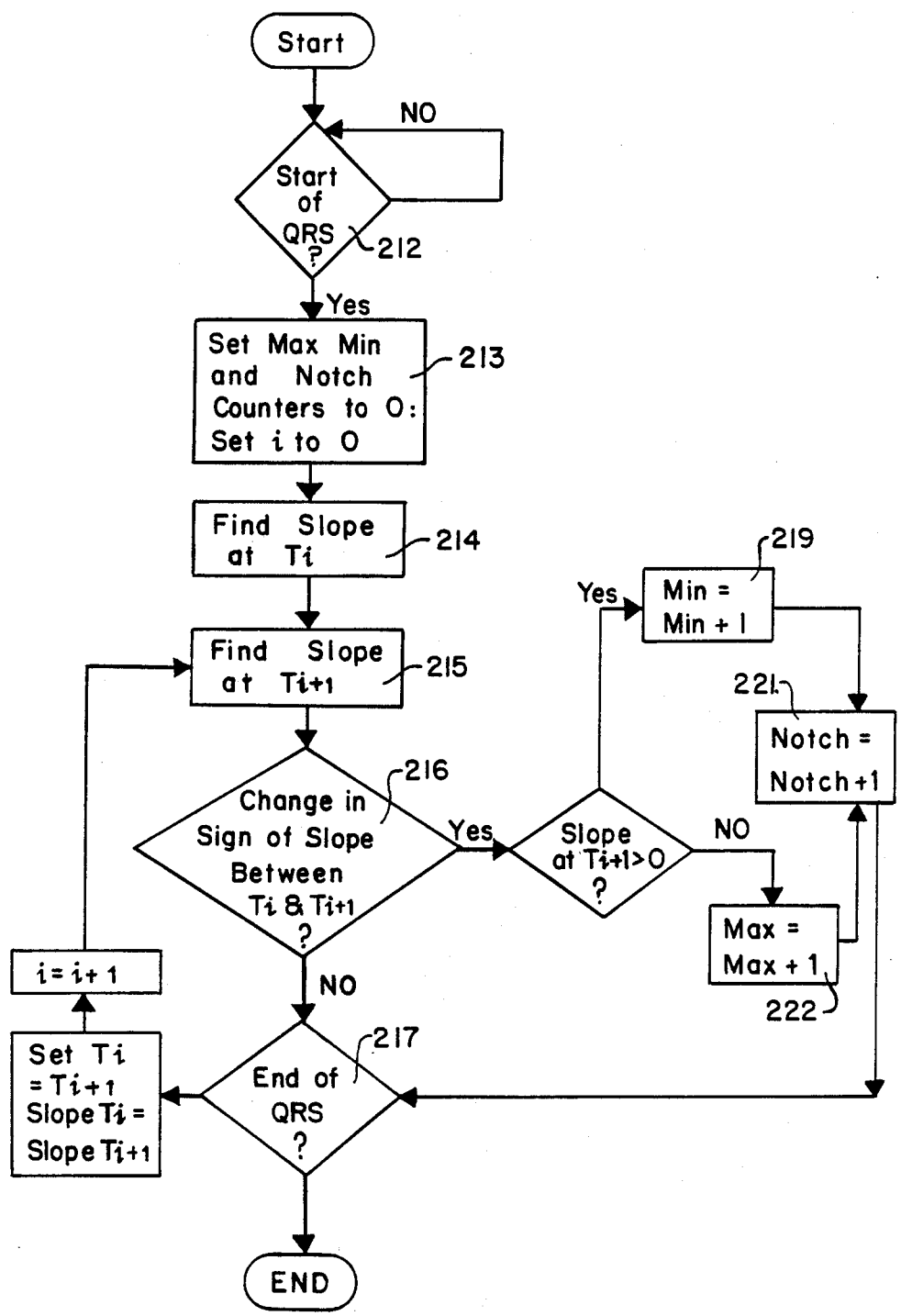

ELECTROCARDIOGRAM ENHANCEMENT SYSTEM AND METHOD

RELATED APPLICATIONS

This is a continuation-in-part of co-pending application titled "Electrocardiogram Enhancement System," U.S. Ser. No. 914,026 filed Oct. 6, 1986 now abandoned which is a continuation-in-part of U.S. Ser. No. 795,059, titled "Sound Enhancement System," filed Nov. 5, 1985 now abandoned.

FIELD OF INVENTION

The system of the present invention relates to the enhancement of electrocardiogram signals. Particularly the system relates to the enhancement of small amplitude, high frequency notches and slurs which are difficult to record on conventional chart recorders and difficult to visually detect within an electrocardiogram waveform by medical personnel.

BACKGROUND OF THE INVENTION

An electrocardiograph records electric potentials generated by the neuromuscular mechanism of the heart. A stimulus arising in the sino-auricular node of the heart sets up a tiny electric current called the excitation or depolarization wave. This wave spreads over the auricular wall and the auricles contract. When the excitation wave is at the junctional tissue between auricle and ventricle, it is delayed by the atrioventricular node at the beginning of the Bundle-of-His. The excitation wave conducts rapidly through the Bundle and then branches to the left and right ventricle.

The excitation wave then conducts slowly through the Purkinje fibers which terminate in the ventricular muscle, causing the ventricles to contract. A period of heart rest follows, after which a fresh impulse arises at the sino-aurircular node and the contraction- cycle once again repeats. By placing electrodes on the chest of a patient, a time varying voltage corresponding to the spreading excitation wave can be measured.

This excitation waveform, referred to as an electrocardiogram (ECG), is used to analyze the operation of the heart. The electrocardiogram is divided up into five time segments, known to those skilled in the art as, P, Q, R, S, and T which correspond to the different parts of the waveform. The "P" or Auricular Wave corresponds to the spread of the wave through the auricular musculature. At the point the wave spreads over the ventricular neural net of the Bundle-of-His, a rapid rise and fall of the wave potential, referred to as the "R" wave occurs. Before the "R" wave portion, a small dip called the "Q" wave occurs in the electrocardiogram while after the "R" wave a large drop in the electrocardiogram occurs called the "S" wave. The final portion of the electrocardiogram, the "T" wave, corresponds to the resting phase of the ventricle during which time an electrical repolarization of the ventricular muscle occurs. After the "T" wave the electrocardiogram reflects a horizontal line or isoelectric baseline indicating a period of heart rest prior to the next cycle of the excitation wave.

By analyzing deviations in the shape of the electrocardiogram, physicians can diagnose pathological conditions which relate to the heart and circulatory system. Typically the electrocardiogram is recorded by a paper chart recorder and examined for deviations in the shape of the various segments of the waveform.

Most chart recorders can accurately record waveforms occurring at frequencies up to 100 Hz. However, waveforms occurring at frequencies greater than 100 Hz are outside the bandwidth of the chart recorder and are distorted or lost when recorded since the changes in the waveform occur too rapidly for the pen or stylus of the chart recorder to follow. For example, conventional ECG chart recorders cannot display the small rapid variations in the waveforms, having frequencies typically in the range of 600 to 1000 Hz, referred to as notches and slurs (hereinafter referred to as "notches") which are common to the QRS complex of patients with clinical and preclinical heart disease.

In one method to overcome the limited bandwidth of an ECG chart recorder, ECG signals are routed for display to a cathode-ray tube. The display generated is then photographed to produce a permanent recording of the waveform. This method is used in research facilities as a research tool and is not readily accessible to cardiologists, internists, and general practitioners outside this environment.

U.S. Pat. No. 4,565,201 describes a signal averaging means which includes a microcomputer programmed to output information indicative of the ECG signal at a fraction of the speed of which it was input to the microcomputer. However, since the notches are small and difficult to detect, cardiologists, internists and other medical personnel cannot detect and analyze the notches with any degree of confidence.

One method to overcome the problem of visual detection and analysis of the notches is to amplify the signal. However since the amplitude of the notches is extremely small, (the ratio of the maximum amplitude of a ECG waveform to the maximum amplitude of a notch may be from 1:50 to 1:20) amplification of the entire waveform to increase the visibility of the notches would drive the signal off scale, saturating the display/recording device. Thus when the signal is amplified to display the notches, the entire ECG waveform cannot be recorded by the chart recorder. In addition, since the notches occur quite frequently near the minimum and maximum amplitudes of the waveform, simultaneous recording of all the notches at the desired amplification is extremely difficult. It has been found that it is preferable that not only the notches, but the entire waveform and the positions of the notches with respect to the waveform be displayed/recorded for proper analysis and diagnosis.

U.S. Pat. No. 3,809,071 describes a means to amplify and display low level signals without saturating the display/recording device. However in this method the larger amplitude signals which are amplified off the scale of the display/recording device are simply cut off at the point of saturation Thus only the small amplitude signals are accurately displayed/recorded.

It is an object of the present invention to provide a means for enhancing electrocardiogram signals such that the waveform may be accurately recorded on a conventional chart recorder.

It is an object of the present invention to provide a means for enhancing electrocardiogram signals in a manner that medical personnel can easily detect and analyze small amplitude, high frequency notches often found in patients with clinical heart disease.

It is an object of the present invention to provide an automatic electrocardiogram enhancement system which is simple for medical personnel to use.

SUMMARY OF THE INVENTION

In the ECG enhancement system of the present invention, small amplitude, high frequency notches associated with myocardial disease and arrhythmias can be recorded by conventional chart recorders. In addition, the notches are clearly visible in the recorded waveform for easy visual detection, inspection and analysis by medical personnel.

In the system of the present invention, ECG signals having small amplitude, high frequency notches are automatically enhanced, first, by selectively amplifying the notches while keeping the amplitude of the remainder of the waveform constant and second, by uniformly expanding the signal in the time domain wherein the inter-component frequency and inter-component phase relationships of the signal are maintained Because the enhancement system of the present invention automatically adjusts the enhancement parameters, the system is simplified and easy to use by medical personnel.

In one embodiment of the present invention, a Fast Fourier Transform (FFT) is performed on the input signal to derive the frequency spectrum of the ECG signals. The frequency components of the spectrum representing the notches are amplified and the entire frequency spectrum is translated into a lower frequency range. The enhanced signal is subsequently transformed back into a time varying signal.

BRIEF DESCRIPTION OF THE DRAWINGS

These and other objects, features and advantages of the present invention will be apparent from the following detailed description of a preferred embodiment of the invention in which:

FIG. 4(a) illustrates the unaltered electrocardiogram signal in the frequency domain.

FIG. 4(b) shows the same signal after the amplitudes of the frequency components representing the notches have been amplified.

FIG. 8 is a flow diagram for a method of detecting and counting notches in the electrocardiogram waveform.

DETAILED DESCRIPTION OF THE DRAWINGS

Figure 1:
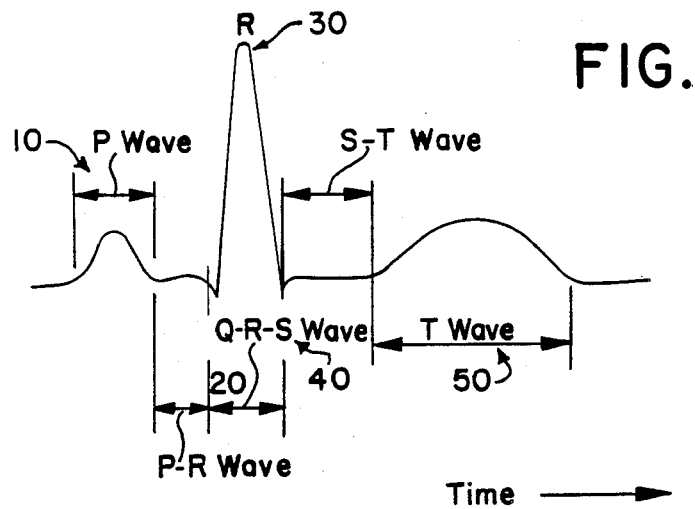
FIG. 1 is an illustration of the time varying waveform that comprises an electrocardiogram.
Figure 2:
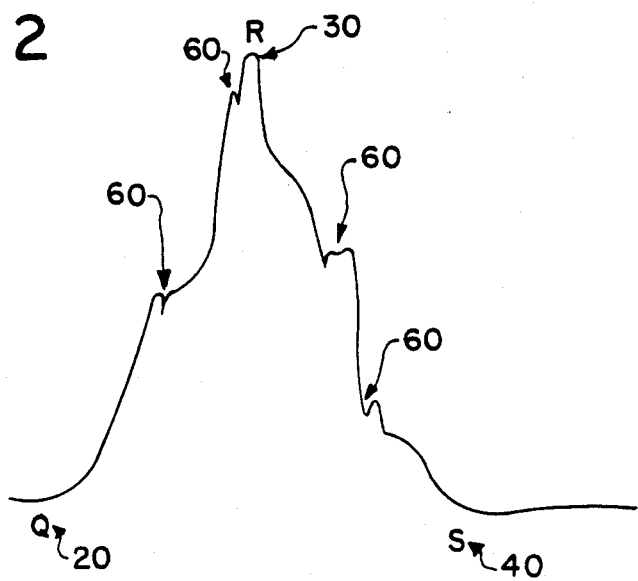
FIG. 2 displays an electrocardiogram where high frequency notches are present.

FIG. 1 shows the waveform of an electrocardiogram which comprises waveform segments "P" 10, "Q" 20, "R" 30, "S" 40, and "T" 50. FIG. 2 shows the high frequency notches 60 that are common in the QRS complex in the case of coronary artery disease. These notches are characterized by small amplitude, rapid time variations that cannot be accurately reproduced by conventional chart recorders.

In order for the ECG waveform to be useful for diagnostic analysis, the high frequency notches must be clearly visible within the waveform so that they can be inspected and analyzed by medical personnel. It is also necessary that the waveform be uniformly translated or expanded in the time domain, to a frequency range within the bandwidth of the chart recorder, in order that the original shape of the waveform (except for the amplified notches) can be accurately recorded on the chart recorder. In other words, each frequency and phase component of the waveform must be consistently modified in order to produce a translated waveform having a frequency range within the bandwidth of the chart recorder, in which the signal component amplitudes, inter-component frequency relationships and inter-component phase relationships among the integral signal components are maintained.

Figure 3A:
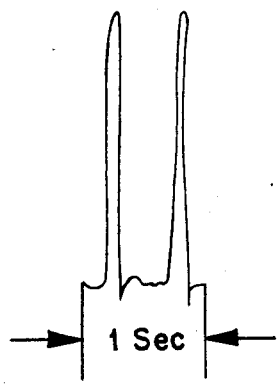
FIG. 3(a) illustrates an unaltered time varying electrocardiogram signal as would be displayed on an Electrocardiograph chart recorder.
Figure 3B:
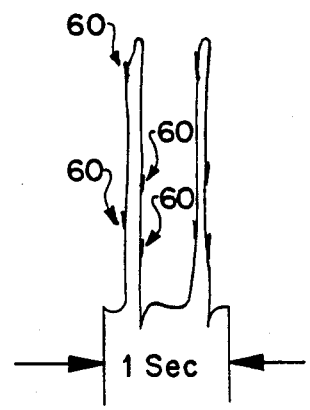
FIG. 3(b) shows the same electrocardiogram signal in which the frequency components representing the notches have been amplified relative to the rest of the signal.
Figure 3C:
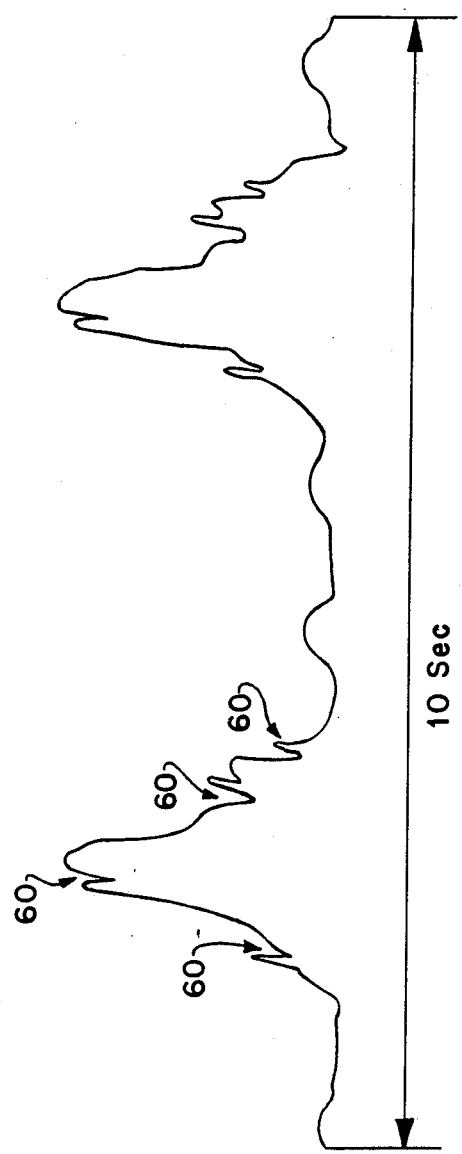
FIG. 3(c) shows the electrocardiogram signal uniformly "expanded" in the time scale.

Through the ECG enhancement system of the invention the original signal, as illustrated in FIG. 3a, is automatically enhanced, first by selectively amplifying the notches 60 without affecting the rest of the waveform, as illustrated in FIG. 3b and, second, by uniformly expanding in the time domain the entire signal, as illustrated in FIG. 3c, in a manner that the high frequency notches 60 can be accurately reproduced by a chart recorder while maintaining the shape of the waveform.

In the present invention, the frequency spectrum of an ECG signal is approximated by calculating the discrete Fourier Transforms (DFT) of the waveform. This is accomplished by an algorithm generally known as a Fast Fourier Transform (FFT) which rapidly makes the computations required to obtain the DFT of an input signal. As a result of the FFT calculations, the frequency spectrum of the input waveform signal is approximated by a series of points or frequency components at different discrete frequencies having amplitudes which correspond to the amplitudes of the input waveform signal at the respective discrete frequencies. Since a set of points defined by discrete frequency, amplitude and phase values result from performing the FFT operation, the sampled frequency spectrum signal obtained using the FFT operation is easily manipulated by performing mathematical operations on these values as discussed in detail below.

The notches which occur in the ECG waveform are very difficult to visually detect and analyze. Therefore it is desirable that these notches be selectively amplified with respect to the remainder of the waveform. In other words selective amplification permits only the notches to be amplified; the remainder of the waveform is not affected. The amplitude of each frequency component with a predetermined frequency range and greater than a minimum amplitude value indicative of notches is multiplied by an amplification factor "H". The value of "H" is selected such that the amplification of the notches is sufficient for visual detection and analysis of the notches, but not too large that the recording device is saturated, that is, the limits of the device are not exceeded. Preferably the value of H is determined by calculating the ratio of the largest amplitude of the frequency components representing the ECG signal, i.e. the "non-notch" frequency components, to the largest amplitude of the frequency components representing the notches, i.e. the notch frequency components, and multiplying the ratio by a gain factor "G" such that the notch is easily discernible without significantly changing the shape of the wave. More particularly, the value of H is determined by calculating the ratio of the largest amplitude of those frequency components up to and including 100 Hz to the largest amplitude of those frequency components greater than 100 Hz and multiplying the ratio by the gain factor G. The gain factor G may be determined empirically based on the waveform. Preferably G ranges from a value greater than zero up to one. Most preferably G is equal to $\frac{1}{4}$.

The frequency range and minimum amplitude value are set such that only the frequency components representing the high frequency notches are amplified. The frequency components representing a notch typically center around frequencies in the range of 600-1000 Hz, while the frequency components representing the remainder of the waveform are below 100 Hz. However, it has been found that the spectrum of frequency components representing a notch may range from 100 to 1500 Hz. Although the frequency components representing a notch may range from 100 to 1500 Hz, it is preferred that the frequency range is greater than 100 Hz up to and including 1200 Hz, thereby accounting for the majority of notch frequency components. The minimum amplitude is selected to exclude high frequency signal noise which can distort the signal. Preferably the minimum amplitude is approximately 5% of the peak amplitude of the notch frequency components, that is, the frequency components above 100 Hz.

Once the frequency components representing the notches are amplified, the frequency spectrum representing the entire waveform is translated to a lower frequency range that is within the bandwidth of the chart recorder. The frequency components are translated or shifted down by dividing the frequency of each of the frequency components by a time scale expansion factor, K. This time scale expansion factor is chosen so that the higher frequency components are translated down to lower frequencies within the bandwidth of the chart recorder while other lower frequency components that are also translated remain within the bandwidth of the chart recorder. The time scale expansion factor may be preselected or, alternatively, may be calculated based upon the highest frequency component detected. For example, if the bandwidth of the chart recorder is 100 Hz and the highest frequency component is 1000 Hz then $K = 1000/100 = 10$.

The translated frequency spectrum is subsequently transformed back into a time varying signal by performing an inverse FFT operation. Since the FFT components comprise both real and imaginary elements, thus taking into account both the frequency and phase elements of the signal, the operation of translating the frequency spectrum does not alter the inter-component phase and inter-component frequency relationships among the components in the spectrum. Therefore, except for the deliberate amplification of the notches, the expanded waveform in the time domain maintains its original shape.

Referring to FIGS. 4a and 4b, the frequency components in the range greater than 100 Hz up to and including 1200 Hz represent notches. Illustratively, A, the peak value of the non-notch frequency components, and $A_2$, the peak value of the notch frequency components have values of 200 mv and 10 mv respectively. Therefore the amplification factor is $H = A_1/A_2 \times G = 200/10 \times \frac{1}{4} = 5$. Thus the frequency components representing the notches in FIG. 4a are increased in amplitude by a factor of 5, as shown in FIG. 4b. The frequency components 100 Hz and below, which represent the remainder of the signal, have not been altered.

Figure 4C:
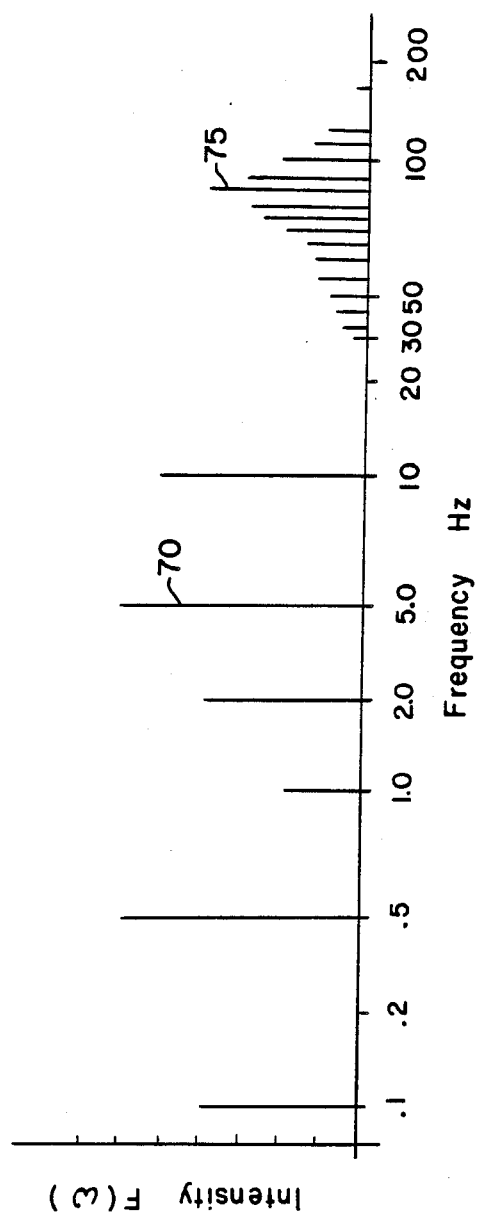
FIG. 4(c) shows the signal after time scale expansion.

The frequency spectrum illustrated in FIGS. 4b is then translated or expanded in the time scale by a factor of 10 as illustrated in FIG. 4c. As can be seen by comparing FIGS. 4b and 4c, the 1000 Hz frequency component in FIG. 4b has been translated so that it is now at 100 Hz in FIG. 4c. Similarly, the frequencies of the remaining components in the signal shown in FIG. 4b are all divided by the time scale expansion factor resulting in the frequency spectrum illustrated in FIG. 4c. Although the time scale expansion factor K used to obtain the frequency spectrum of FIG. 4c from that shown in FIG. 4b is equal to 10, this value for K is only used as an example and other values for K can be used.

The inter-component phase and inter-component frequency relationships remain equivalent. As shown in FIG. 4b, the 50 Hz and 100 Hz components are separated by one octave. In FIG. 4c, the respective translated frequency components, at 5 Hz and 10 Hz, are also separated by one octave. Thus, the inter-component frequency and inter-component phase relationships in the signal are maintained in the enhanced signal after the entire frequency spectrum of the signal is translated into a range suitable for accurate reproduction of the signal on a conventional chart recorder.

Figure 5:
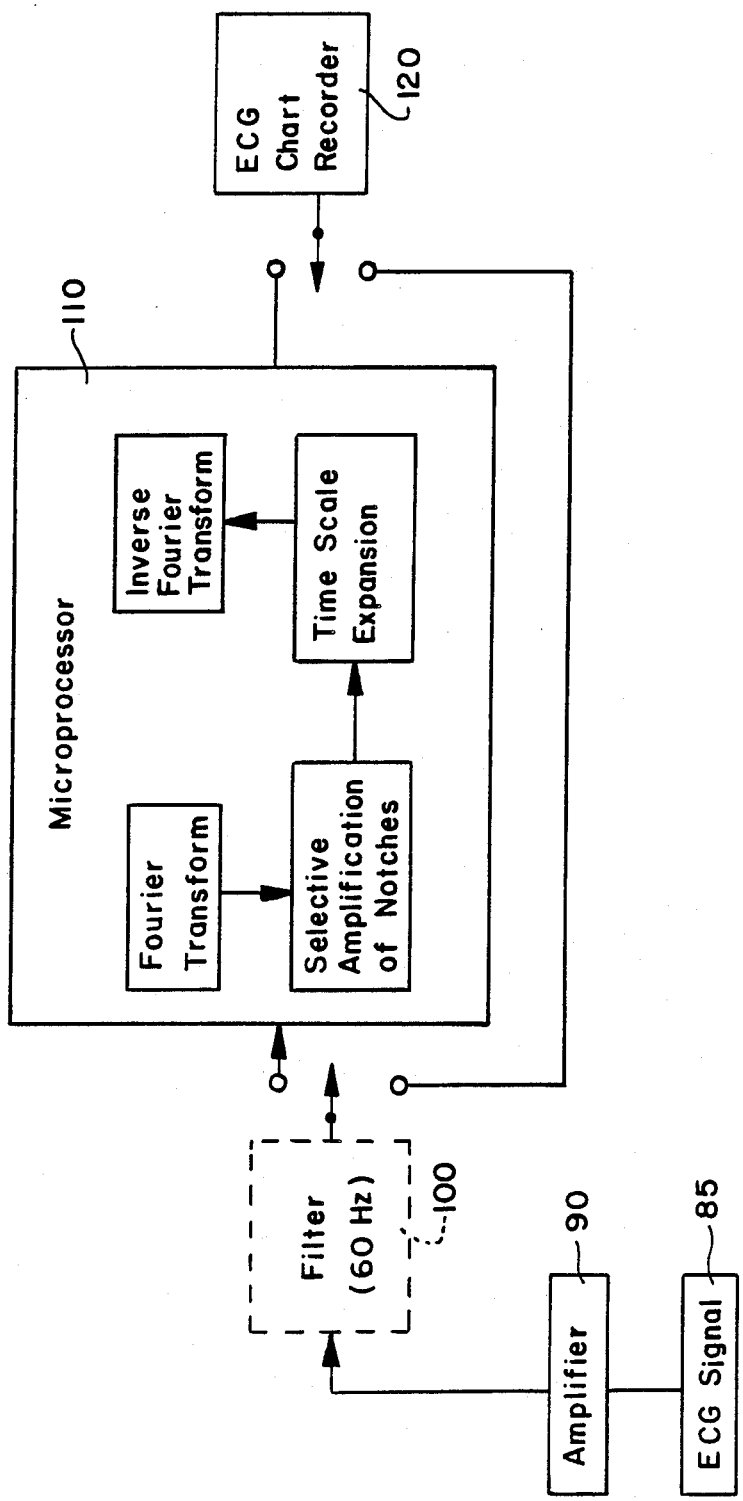
FIG. 5 is a block diagram of an embodiment of the ECG enhancement system of the present invention.

FIG. 5 is a schematic diagram of an embodiment of the ECG enhancement system of the present invention in which an electrical signal generated by the heart is detected, amplified and input to a microprocessor. There the frequency components representing the notches are selectively amplified and the time scale of the entire signal is then uniformly expanded or translated so that the processed signal can be reproduced accurately on a conventional chart recorder.

More particularly, a series of electrodes are placed on the surface of the chest of the patient. The potential generated by heart contractions is then measured between a selected pair of electrodes. The measured signal 85 is amplified by amplifier 90 so that the entire signal comprising the electrocardiogram is amplified for processing. The amplified signal is then preferably passed through a 60 Hz filter 100 to remove any interference typically at 60 Hz in the signal due to the surrounding environment. The signal is then input to a microprocessor 110 where a Fourier Transform of the signal is generated, the frequency components representing the notches are selectively amplified, the time scale of the entire frequency spectrum of the signal is uniformly expanded and an inverse Fourier Transform is performed to output a time varying signal. The signal output is sent to a chart recorder 120 for accurate reproduction of the enhanced ECG signal.

As discussed in detail below with reference to the flow diagram shown in FIGS. 6a and 6b, the microprocessor 110 performs a number of mathematical operations on the ECG signal to selectively enhance the amplitude of the frequency components representing notches and to uniformly expand the ECG waveform in the time scale. Among the operations that the microprocessor 110 performs are analog to digital conversion of the signal, signal sampling, Fourier transform, amplification of the amplitudes of the frequency components representing the notches, time scale expansion, inverse Fourier transform, digital to analog conversion, and storage of the information in temporary and permanent memory. Alternatively, analog to digital and digital to analog signal conversion can be performed external to the microprocessor. Illustratively, the microprocessor 110 is a CMOS microprocessor such as the 8 bit MC68HC11A4 microprocessor manufactured by Motorola Inc. of Schaumburg, Ill., although other devices with similar capabilities can be used.

Figure 6A:
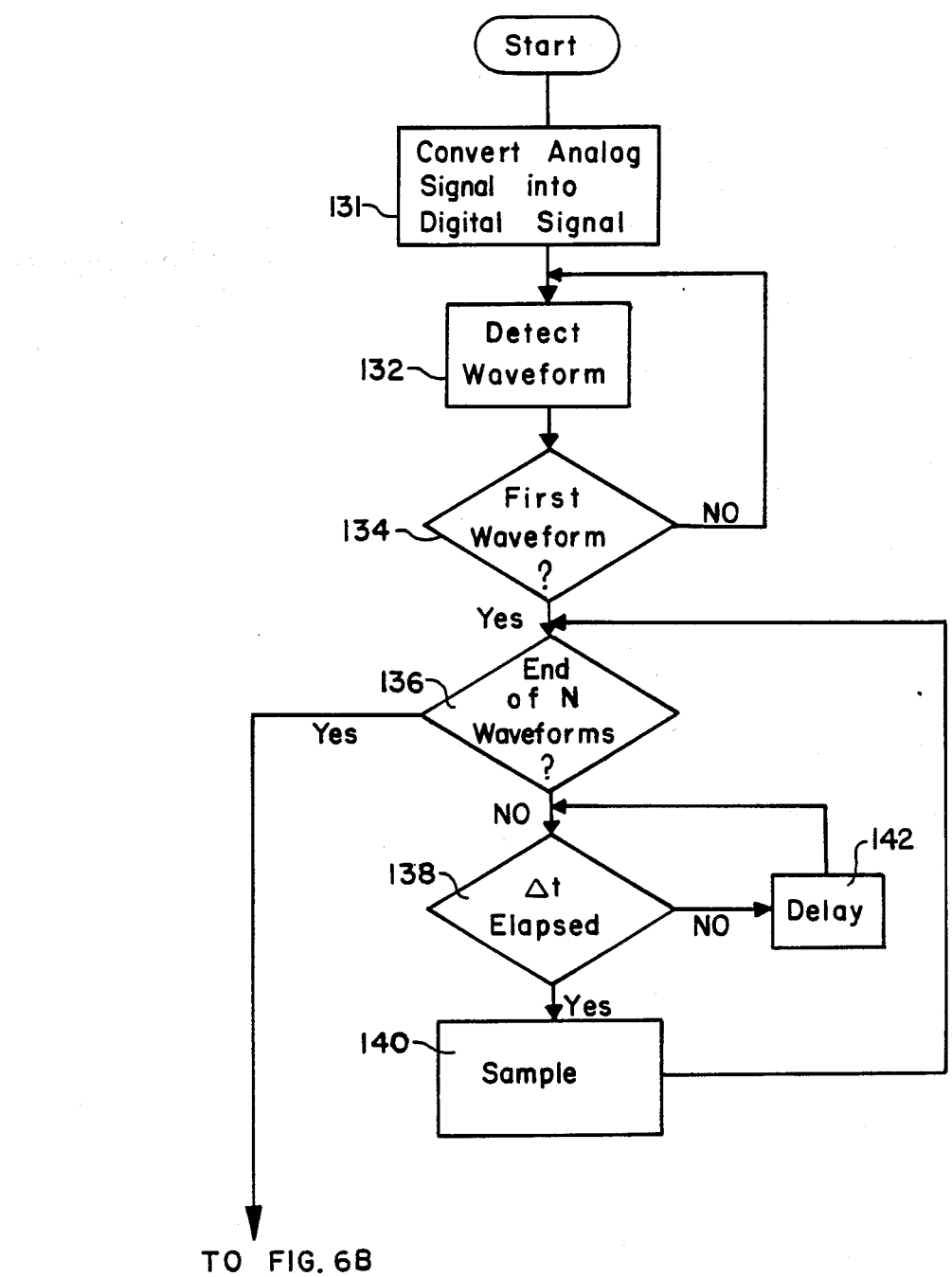
FIGS. 6(a) and 6(b) is a flow diagram illustrating an embodiment of the electrocardiogram enhancement system of the present invention.
Figure 6B:
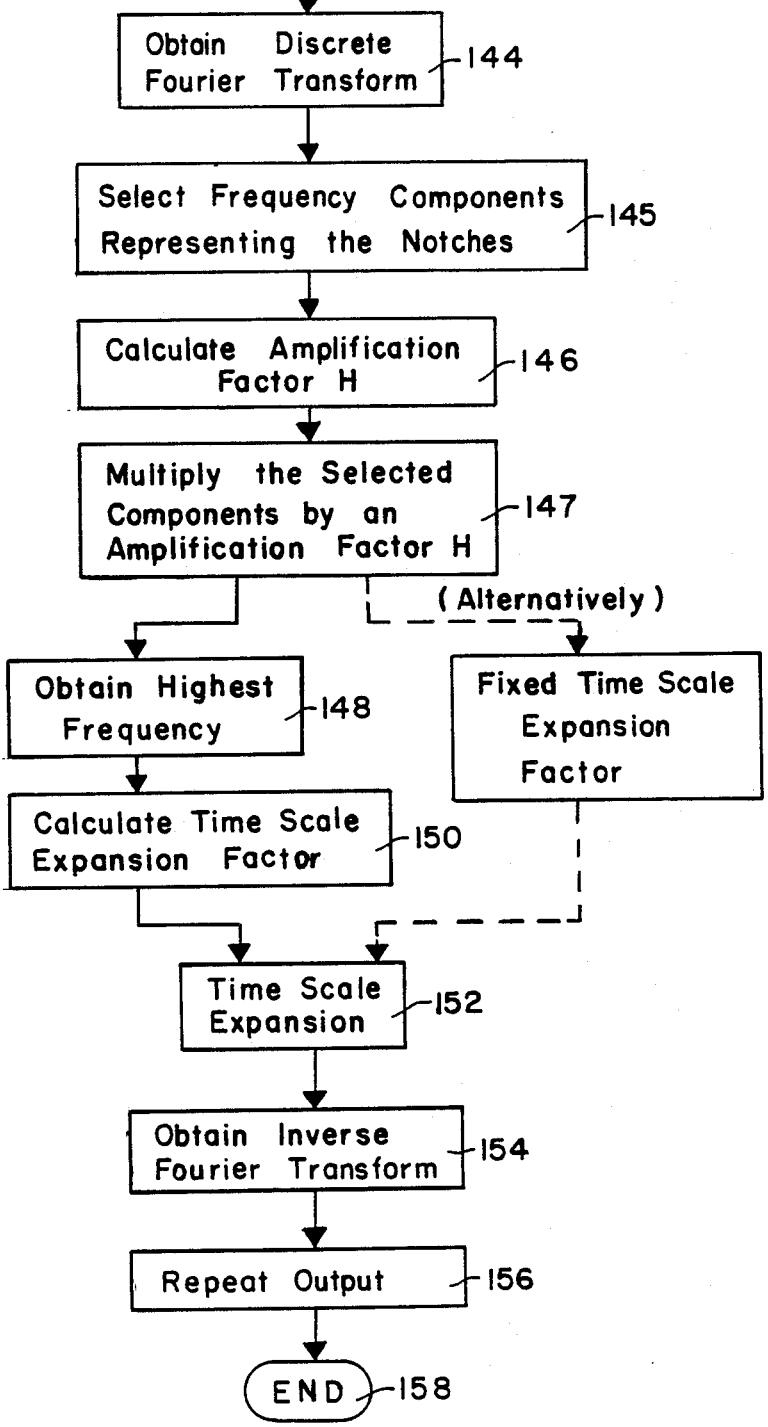

FIGS. 6a and 6b together show a flow diagram describing the operation of the microprocessor of the embodiment of the present invention illustrated in FIG. 5. The amplified ECG signal is received by the microprocessor and converted from an analog signal to a digital signal in block 131.

In blocks 132, 134 the start of the ECG waveform is determined. Preferably the beginning of this waveform is determined automatically. A peak detector is used to determine the maximum amplitude of the ECG waveform which occurs at the peak of the "R" wave. The threshold level of a threshold detector is then set an arbitrary amount below this maximum amplitude. When the signal amplitude exceeds the threshold level, a pulse is generated which triggers a time delay having a duration approximately equal to the expected time period between heart pulses. Illustratively, the duration of the time delay is about 750 milliseconds. The time delay is used to inhibit the operation of the threshold detector until the beginning of the next heart pulse. Preferably, the duration of the delay is automatically adjusted to accommodate different pulse rates by setting the time delay to a duration less than the pulse rate. The time delay generator and threshold detector are synchronized to insure operation at the appropriate times such that every time another ECG waveform is detected, another trigger pulse is automatically generated. A counter is used to count the number of ECG waveforms for sampling.

In block 136, it is determined if a predetermined number "N" of ECG waveforms, corresponding to the number of trigger pulses generated by exceeding the threshold of the threshold detector, have been detected by the ECG waveform counter. If N pulses have not been detected, in block 138 it is determined whether the input electrical signal was sampled (in block 140) within the last dT seconds. If the previous ECG waveform sampling occurred within the last dT seconds, the sampling of the waveform is delayed a fixed period of time as shown by block 142. If the previous ECG waveform sampling occurred more than dT seconds previously, the input electrical signal is sampled as shown by block 140 and the amplitudes of the stored waveform are stored in the memory portion of the microprocessor. As a result of the sampling loop of blocks 136, 138, 140 and 142, the input electrical signal comprising the N ECG waveforms is sampled every dT seconds and a sampled input signal is obtained. Illustratively, dT is equal to 20 microseconds although other values for dT can be chosen. The microprocessor initiates the process again and re-determines in block 136 whether N waveforms have been detected.

After N waveforms have been detected, a signal corresponding to the frequency spectrum of these sampled waveforms is obtained, by calculating the fast Fourier transform (FFT) of the waveform, in block 144 as shown in FIG. 6b and is stored in the memory of the microprocessor.

In block 145, all components of the frequency spectrum which lie in the range greater than 100 up to and including 1200 Hz are examined. The frequency components in this range which are greater than 5% of the peak amplitude of the notch frequency components are typically representative of notches. In Block 146 the amplification factor H is automatically calculated by the microprocessor to be equal to the ratio of the peak amplitude of the non-notch frequency components to the peak amplitude of the frequency components multiplied by the gain factor G. The selected frequency components are multiplied by the amplification factor H, as shown in Block 147.

The signal may be translated or expanded on the time scale if each discrete FFT frequency value or component is divided by the time scale expansion factor K. This time scale expansion factor is chosen so that the most rapid time variations of the ECG waveform (the notches) will be slowed down to the point that a chart recorder pen can accurately follow and reproduce the waveform. The time scale expansion factor may be calculated for a particular waveform or a fixed time scale expansion factor may be used. In block 148 the highest frequency value of the waveform is obtained and the time scale expansion factor is calculated in block 150 by determining the value which will bring the highest frequency component into the bandwidth of the chart recorder.

In block 152, each frequency component of the sampled frequency spectrum is divided by the time scale expansion factor K. A time varying output electrical signal is obtained from the translated frequency spectrum in block 154 by performing an inverse FFT operation on the signal.

The enhanced time varying signal is optionally repeated a number of times as shown in box 156, repeat output. The signal is then converted from a digital to analog signal and sent to the ECG recorder for subsequent recording of the signal.

The operations performed by microprocessor 110 can be described mathematically. If the original time varying input signal is f(t), its frequency spectrum as shown in FIG. 4a is F($\omega$) and the amplified frequency spectrum is F'($\omega$) then $$F'(\omega) = HF(\omega) \qquad (1)$$

where H is the amplification factor.
Mathematically, $$F(\omega) = \int_{-\infty}^{+\infty} f(t) e^{-j\omega t} dt \qquad (2)$$

Upon multiplying f(t) by an amplification factor H, the Fourier Transform becomes $$\int_{-\infty}^{+\infty} Hf(t) e^{-j\omega t} dt \qquad (3)$$

Hence amplitudes of all frequency components are multiplied by the amplification factor H. Thus, multiplying the amplitude of all the frequency components of the Fourier Transform by factor H will result in Hf(t) when the inverse transform is taken:

$$\frac{1}{2\pi} \int_{-\infty}^{+\infty} H F(\omega) e^{j\omega t} d\omega = \quad (4)$$

$$\frac{H}{2\pi} \int_{-\infty}^{+\infty} F(\omega) e^{j\omega t} d\omega \quad (5)$$

thus, $$f'(t) = Hf(t) \quad (6)$$

Similarly, if the original time varying signal is f(t), its frequency spectrum is F($\omega$), and the translated frequency spectrum signal if F'($\omega$) then, $$F'(\omega) = F(K\omega) \quad (7)$$

where K is the time scale expansion factor.

As is known from algebra, in order to translate the frequency spectrum F($\omega$) by dividing the number corresponding to each frequency by K, $\omega$ in the expression must be multiplied by K as in equation (7) above.

By using the inverse Fourier transfer operation, the time varying output signal f'(t) corresponding to the translated frequency spectrum signal F'($\omega$) is therefore:

$$f'(t) = \frac{1}{2\pi} \int_{-\infty}^{+\infty} F'(\omega) e^{j\omega t} d\omega \quad (8)$$

substituting equation (7) into equation (8) results in the following:

$$f'(t) = \frac{1}{2\pi} \int_{-\infty}^{+\infty} F(\omega K) e^{j\omega t} d\omega \quad (9)$$

If $\omega' = K\omega$, $d\omega = 1/K d\omega'$, and $$f'(t) = \frac{1}{2\pi} \int_{-\infty}^{+\infty} F(\omega') e^{\frac{j\omega' t}{K}} \frac{d\omega'}{K} \quad (10)$$

Taking the inverse Fourier transform of the right side of equation (10) results in the following:

$$f'(t) = \frac{1}{K} f\left(\frac{1}{K} t\right) \quad (11)$$

Therefore, when each frequency component of the original time varying signal is translated in time scale by dividing each component by factor K, and if K is greater than one, the resulting time varying output signal is equivalent to the time varying input signal expanded in time by a factor of K. Note additionally that the output wave f(t/K) has the exact shape of f(t) except for the time scale expansion.

It follows with respect to the high frequency notches that the enhanced signal f'(t) is equal to Hf'(t/K) and the remainder of the waveform is equal to f'(t/K).

Figure 7:
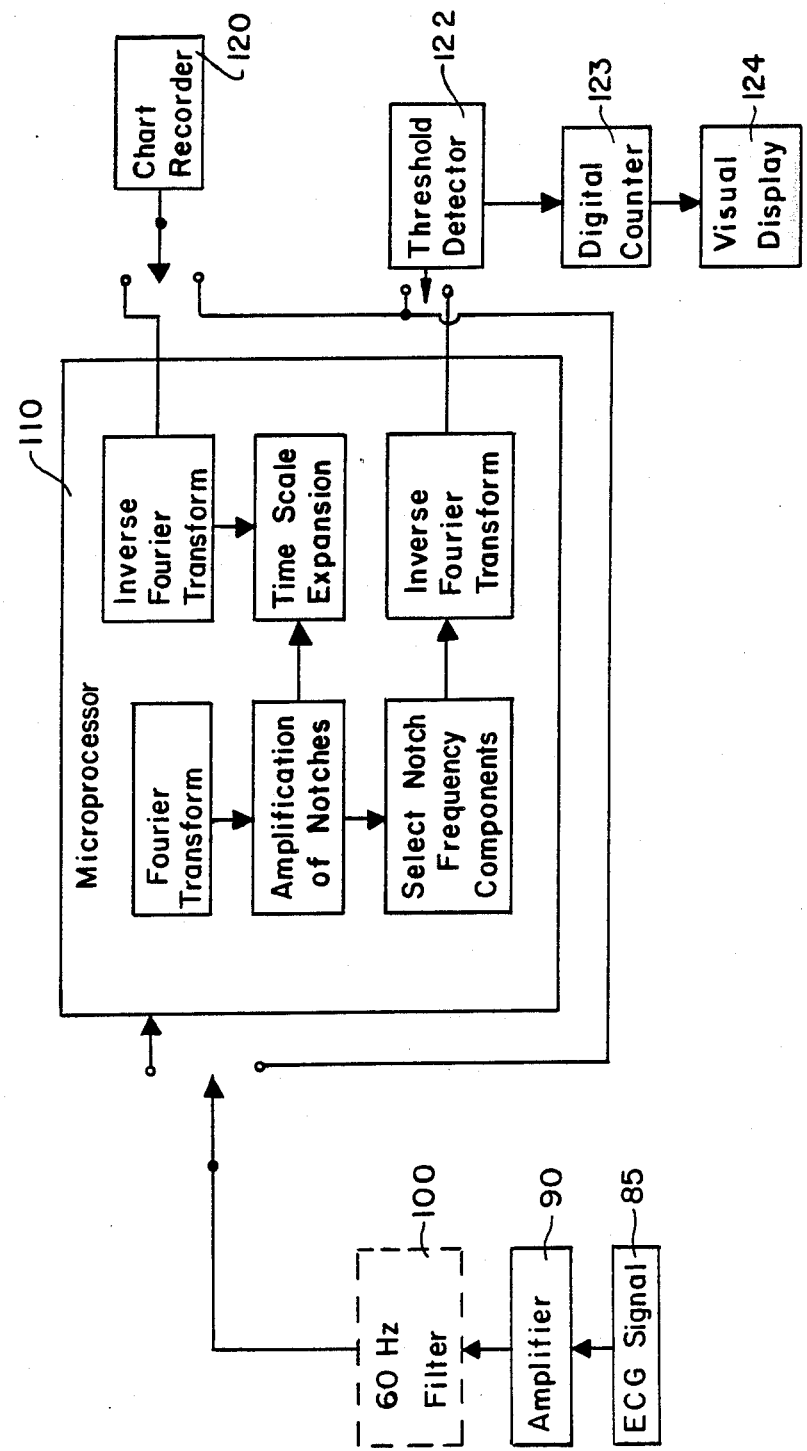
FIG. 7 is a block diagram of an apparatus for detecting and counting notches in the electrocardiogram waveform.

Another embodiment of the present invention, is illustrated in FIG. 7. The electrical signal generated by the heart is measured at 85, and amplified by amplifier 90. The signal is then preferably passed through a 60 Hz filter 100 to remove any interference typically at 60 Hz in the signal due to the surrounding environment. The signal is subsequently input to microprocessor 110. In the microprocessor the signal is converted from an analog to digital signal, a Fourier transform of the signal is generated, the frequency components representing the notches are amplified, the time scale of the entire frequency spectrum of the signal is uniformly expanded and an inverse Fourier transform and digital-to-analog conversion are performed to output a time varying signal to be output to the chart recorder 120 for accurate recording of the signal. In addition, after selective amplification of the notches, an inverse Fourier transform of the notch portion of the signal is generated and output to a threshold detector 122 for the detection of those notches of a predetermined minimum amplitude. The output pulse of the threshold detector 122 is counted by a digital counter 123 and output to a numeric display 124.

Alternatively, as described in the flow diagram of FIG. 8, digital techniques involving the determination of the first derivative of the signal waveform and the count of the number of zero crossings of the first derivative that occur within a certain time span can be used to detect notches or slurs.

The beginning of the QRS wave is first detected in block 212 and the minima, maxima and notch counters are initialized in block 213. The slopes at a predetermined time $t_i$ and $t_{i+1}$ are calculated in blocks 214, 215 and compared in block 216. A change in the sign of the slope indicates a zero crossing in block 217. If the sign of the slope at test point $t_i$ and test point $t_{i+1}$ are the same, the next test of the signal is taken at block 218 and the slopes calculated and compared with the last slope value. If the sign of the slopes at $t_i$ and $t_{i+1}$ are not the same and the slope at $t_{i+1}$ is less than zero, the maxima counter is incremented by one in block 222 and the notch counter is incremented by one in block 221. If the slope at $t_{i+1}$ is greater than or equal to zero, the minima counter in block 219 as well as the notch counter in block 221 are incremented by one. $T_i$ and the slope at $t_i$ are set equal to $t_{i+1}$ and the slope at $t_{i+1}$ respectively in block 220. The slope at the next test point is then calculated and compared. This process continues until the end of the QRS wave is detected in block 217. The notch, minima, and maxima counts are used by physicians to analyze coronary artery disease and arrhythmia.

The time between tests for determining the first derivative of the signal, i.e., the difference in time between $t_i$ and $t_{i+1}$, is a fixed amount of time which is preferably determined empirically. An illustrative frequency is 800 Hz. However, this does not imply that the sampling rate of the signal used in one embodiment of the present invention must be equal to the testing rate for determination of the first derivative. Illustratively the signal may be sampled at a rate of 5000 Hz and tested for the derivative of the signal at a rate of 1000 Hz. sampled at a rate of 5000 Hz and tested for the derivative of the signal at a rate of 1000 Hz. While the invention has been described in conjunction with specific embodiments, it is evident that numerous alternatives, modification, variations and uses will be apparent to those skilled in the art in light of the foregoing description.

We claim:

1. A method for enhancing an electrocardiogram signal having frequency, low amplitude notches that are difficult to visually detect within an electrocardiogram signal waveform and that have frequencies above the signal recording bandwidth of a conventional chart recorder, said signal having a plurality of frequency components, each frequency component having a frequency, phase and amplitude, the frequencies of the frequency components comprising a first inter-component frequency relationship and the phases of the frequency components comprising a first inter-component phase relationship said enhancement method comprising the steps of:

selectively amplifying frequency components representing the notches relative to other frequency components in the electrocardiogram signal; and expanding said electrocardiogram signal including the amplified frequency components in time scale by a time scale expansion factor, frequency components representing said expanded signal having a second intercomponent frequency relationship and a second inter-component phase relationship equivalent to said first inter-component frequency relationship and first inter-component phase relationship, said expanded signal having a frequency range within the bandwidth of a conventional chart recorder.

2. The method of claim 1 wherein said expanding of said electrocardiogram signal in the time scale comprises dividing the frequency of each frequency component by a time scale expansion factor.

3. The method of claim 2 wherein said time scale expansion factor is greater than one.

4. The method of claim 1 wherein said selectively amplifying said electrocardiogram signal comprises:

selecting those frequency components of the electrocardiogram signal within a predetermined frequency range and greater than a minimum amplitude value indicative of notches; and multiplying each of the selected frequency components by an amplification factor.

5. The method of claim 4 wherein said frequency range is greater than 100 up to and including 1200 Hz.

6. The method of claim 4 wherein said minimum amplitude value is determined to exclude high frequency signal noise.

7. The method of claim 6 wherein said minimum amplitude value is greater than 5% of the peak amplitude of notch frequency components.

8. The method of claim 4 wherein the amplification factor is equal to the ratio of a peak amplitude of non-notch frequency components to a peak amplitude of the notch frequency components multiplied by a gain factor.

9. The method of claim 8 where the gain factor ranges from a value greater than zero up to one.

10. The method of claim 1 further comprising:

generating a Fourier transform of the electrocardiogram signal to obtain a frequency spectrum comprising the frequency components representing the electrocardiogram signal; and generating an inverse Fourier transform of the frequency spectrum after selectively amplifying and expanding the frequency component of the signal.

11. The method of claim 1 further comprising the step of accurately recording the expanded signal and displaying the high frequency, low amplitude notches.

12. A method for enhancing an electrocardiogram signal in a first frequency range having high frequency, low amplitude notches that are difficult to visually detect and analyze within an electrocardiogram signal waveform and that have frequencies above the signal recording bandwidth of a conventional chart recorder, said enhancement method comprising the steps of:

performing a Fourier transform operation upon the electrocardiogram signal whereby a frequency spectrum signal is obtained, said frequency spectrum signal comprising frequency components having an amplitude, frequency, and phase, the frequencies of the frequency components comprising a first inter-component frequency relationship and the phases of the frequency components comprising a first inter-component phase relationship;

selecting frequency components within a predetermined frequency range and greater than a minimum amplitude value that are indicative of notches;

amplifying each of the selected frequency components by an amplification factor;

expanding the frequency spectrum signal in time scale by dividing each frequency component by a time scale expansion factor, frequency components having a second inter-component frequency and second inter-component phase relationship equivalent to said first inter-component frequency and first inter-component phase relationship; and performing an inverse Fourier transform operation upon the expanded frequency spectrum signal to obtain an enhanced electrocardiogram signal, said enhanced electrocardiogram signal having a frequency range within the signal recording bandwidth of conventional chart recorders.

13. The method of claim 12 wherein said time scale expansion factor is greater than one.

14. The method of claim 12 wherein said amplification factor is a value equal to the ratio of a peak amplitude of non-notch frequency components to a peak amplitude of the notch frequency components multiplied by a gain factor.

15. The method of claim 14 wherein said gain factor ranges from a value greater than zero up to one.

16. The method of claim 12 wherein said frequency range is greater than 100 up to and including 1200 Hz.

17. The method of claim 12 wherein said minimum amplitude value is determined to exclude high frequency signal noise.

18. The method of claim 17 wherein said minimum amplitude value is greater than 5% of the peak value of the notch frequency components.

19. The method of claim 12 further comprising the step of accurately recording the enhanced electrocardiogram waveform and displaying the high frequency, low amplitude notches.

20. Apparatus for enhancing an electrocardiogram signal having high frequency, low amplitude notches that are difficult to visually detect within an electrocardiogram signal waveform and that have frequencies above the signal recording bandwidth of a conventional chart recorder, said signal having a plurality of frequency components, each frequency component having a frequency, phase and amplitude, the frequencies of the frequency components comprising a first inter-component frequency relationship and the phases of the frequency components comprising a first inter-component phase relationship, said apparatus comprising:

means for selectively amplifying frequency components representing the notches relative to other frequency components in the electrocardiogram signal; and means for expanding said electrocardiogram signal including the amplified frequency components in time scale by a time scale expansion factor, frequency components representing said expanded signal having a second inter-component frequency relationship and second inter-component phase relationship equivalent to said first inter-component frequency relationship and first inter-component phase relationship, said expanded signal being within the bandwidth of a conventional chart recorder, whereby the expanded signal is accurately recorded, and the high frequency, low amplitude notches are made visible 21. The apparatus of claim 20 wherein the means for expanding said electrocardiogram signal in the time scale comprises a means for dividing the frequency of each frequency component by a time scale expansion factor.

22. The apparatus of claim 21 wherein said time scale expansion factor is greater than one.

23. The apparatus of claim 20 wherein the means for selectively amplifying said electrocardiogram signal comprises:
means for selecting frequency components within a predetermined frequency range and greater than a minimum amplitude value indicative of notches; and
means for amplifying each of the selected frequency components by an amplification factor.

24. The apparatus of claim 23 wherein said frequency range is greater than 100 up to and including 1200 Hz.

25. The apparatus of claim 23 wherein said amplitude range excludes high frequency signal noise.

26. The apparatus of claim 25 wherein said minimum amplitude value is equal to 5% of the peak value of the notch frequency components.

27. The apparatus of claim 23 wherein said amplification factor is equal to the ratio of a peak amplitude of non-notch frequency components to a peak amplitude of the notch frequency components multiplied by a gain factor.

28. The apparatus of claim 27 wherein said gain factor ranges from a value greater than zero up to one.

29. The apparatus of claim 20 further comprising:
means for generating a Fourier transform of the electrocardiogram signal to obtain a frequency spectrum comprising the frequency components representing the electrocardiogram signal; and
means for generating an inverse Fourier transform of the frequency spectrum after selectively amplifying and expanding in the time scale the frequency components of the signal.

30. The apparatus of claim 29 wherein the means for generating a Fourier transform, means for selectively amplifying, means for expanding and means for generating an inverse Fourier transform comprises a microprocessor.

31. The apparatus of claim 20 further comprising a means for counting the high frequency notches and a means for displaying said count of notches.

32. The apparatus of claim 31 wherein the means for counting the notches comprises:
means for detecting the beginning and end of a QRS wave of the electrocardiogram signal waveform;
means for calculating the slope of the waveform at a first test point;
means for calculating the slope of the waveform at a second subsequent test point, said second test point being a predetermined time period after said first test point;
means for comparing the slopes of said first and second test points;
means for incrementing a notch counter if the signs of said slopes of said test points are not equal;
means for setting said first test point equal to said second test point wherein the means for calculating the slope of the waveform at the second test point, means for comparing the slopes of said first and second test points and means for incrementing said notch counter continue to operate to sequence until the end of the QRS wave is detected.

33. The apparatus of claim 31 wherein the means for counting the notches comprises:
a threshold detector which generates an output pulse upon detection of those notches of a predetermined minimum amplitude;
means for inputting selected frequency components indicative of notches to the threshold detector; and
a digital counter which counts the output pulses of the threshold detector.

34. The apparatus of claim 20 further comprising a chart recording device for the display of said expanded signal whereby the electrocardiogram signal is accurately recorded and the high frequency, low amplitude notches are visible in the displayed signal.

35. The apparatus of claim 20 further comprising means for accurately recording the expanded signal and means for displaying the high frequency, low amplitude notches.

36. Apparatus for enhancing an electrocardiogram signal in a first frequency range having high frequency, low amplitude notches that are difficult to visually detect and analyze within a electrocardiogram signal waveform and that have frequencies above the signal recording bandwidth of a conventional chart recorder comprising:
means for performing a Fourier transform operation upon the electrocardiogram signal whereby a frequency spectrum signal is obtained, said frequency spectrum signal comprising frequency components having an amplitude, frequency, and phase, the frequencies of the frequency components comprising a first inter-component frequency relationship and the phases of the frequency components comprising a first inter-component phase relationship;
means for selecting frequency components within a predetermined frequency range and greater than a minimum amplitude value that are indicative of notches;
means for amplifying each of the selected frequency components by an amplification factor;
means for expanding the frequency spectrum in time scale by dividing each frequency component by a time scale expansion factor, frequency components having a second inter-component frequency relationship and a second inter-component phase relationship equivalent to said first inter-component frequency relationship and first inter-component phase relationship;
means for performing an inverse Fourier transform operation upon the expanded frequency spectrum signal to obtain an enhanced electrocardiogram signal, said enhanced electrocardiogram signal having a frequency range within the bandwidth of conventional chart recorders; and chart recording means for display of the expanded signal where in the high frequency, low amplitude notches are visible within the displayed signal.

37. The apparatus of claim 36 wherein the means for performing a Fourier transform, means for selecting frequency components, means for amplifying the selected frequency components, means for expanding the frequency spectrum and means for performing an inverse Fourier transform comprises a microprocessor.

38. The apparatus of claim 36 wherein said time scale expansion factor is greater than one.

39. The apparatus of claim 36 wherein said amplification factor is equal to the ratio of a peak amplitude of non-notch frequency components to a peak amplitude of the notch frequency components multiplied by a gain factor.

40. The apparatus of claim 39 wherein said gain factor ranges from a value greater than zero up to one.

41. The apparatus of claim 36 wherein said frequency range is greater than 100 up to and including 1200 Hz.

42. The apparatus of claim 36 wherein said minimum amplitude value excludes high frequency signal noise.

43. The apparatus of claim 42 wherein said minimum amplitude value is 5% of the peak value of the notch frequency components.

44. A method for enhancing an electrocardiogram signal having high frequency, low amplitude notches that have frequencies above 100 Hz and are difficult to visually detect within an electrocardiogram signal waveform, said signal having a plurality of frequency components, each frequency component having a frequency, phase and amplitude, said enhancement method comprising the steps of:

amplifying the frequency components above 100 Hz relative to other frequency components in the electrocardiogram signal by an amplification factor; and then expanding said electrocardiogram signal including the amplified frequency components in time scale by a time scale expansion factor to produce an expanded signal, said expanded signal having frequency components in which the frequencies are those of the frequency components of the electrocardiogram signal divided by the time scale expansion factor, said expanded signal having a frequency range within the bandwidth of a conventional chart recorder.

45. The method for enhancing an electrocardiogram signal of claim 44 wherein said frequencies of the frequency components of the electrocardiogram signal comprise a first inter-component relationship and the phases of the frequency components comprise a first inter-component phase relationship and frequencies of the frequency components of the expanded signal comprise a second inter-component frequency relationship equivalent to said first inter-component frequency relationship and the phases of the frequency components comprise a second inter-component phase relationship equivalent to said first inter-component phase relationship.

46. The method for enhancing an electrocardiogram signal of claim 44 further comprising:

generating a Fourier transform of the electrocardiogram signal to obtain a frequency spectrum comprising the frequency components representing the electrocardiogram signal; and generating an inverse Fourier transform of the frequency spectrum after amplifying and expanding the signal.

47. The method of claim 44 further comprising displaying the high frequency, low amplitude notches.

48. Apparatus for enhancing an electrocardiogram signal having high frequency, low amplitude notches that have frequencies above 100 Hz and are above the signal recording bandwidth of a conventional chart recorder and difficult to visually detect within an electrocardiogram signal waveform, said signal being within a first frequency range and having a plurality of frequency components, each frequency component having a frequency, phase and amplitude, said apparatus comprising:

means for amplifying the frequency components above 100 Hz relative to other frequency components in the electrocardiogram signal by an amplification factor; and means for expanding said electrocardiogram signal including the amplified frequency components in time scale by a time scale expansion factor to produce an expanded signal, said expanded signal having frequency components in which the frequencies are those of the frequency components of the electrocardiogram signal divided by the time scale expansion factor, said expanded signal having a frequency range within the bandwidth of a conventional chart recorder.

49. The apparatus of claim 48 wherein said frequencies of the frequency components of the electrocardiogram signal comprise a first inter-component frequency relationship and the phases of the frequency components comprise a first inter-component phase relationship and frequencies of the frequency components of the expanded signal comprise a second inter-component frequency relationship equivalent to said first inter-component frequency relationship and the phases oaf the frequency components comprise a second inter-component phase relationship equivalent to said first inter-component phase relationship.

50. The apparatus of claim 48 further comprising:

means for generating a Fourier transform of the electrocardiogram signal to obtain a frequency spectrum comprising frequency components representing the electrocardiogram signal; and means for generating an inverse Fourier transform of the frequency spectrum after amplifying and expanding the signal.

51. The apparatus of claim 48 further comprising a chart recording device for the display of said expanded signal whereby the electrocardiogram signal is accurately recorded and the high frequency, low amplitude notches are visible in the displayed signal.

52. The apparatus of claim 48 further comprising means for displaying the high frequency, low amplitude notches.

* * * * *